United States Patent
Nozato et al.

(10) Patent No.: US 7,954,948 B2
(45) Date of Patent: Jun. 7, 2011

(54) OPTICAL TOMOGRAPHIC IMAGING METHOD AND APPARATUS

(75) Inventors: Koji Nozato, Yokohama (JP); Mitsuro Sugita, Tokyo (JP); Futoshi Hirose, Yokohama (JP); Akihiro Katayama, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/636,607

(22) Filed: Dec. 11, 2009

(65) Prior Publication Data

US 2010/0165289 A1 Jul. 1, 2010

(30) Foreign Application Priority Data

Dec. 26, 2008 (JP) ................. 2008-331879

(51) Int. Cl.
*A61B 3/14* (2006.01)
(52) U.S. Cl. ......... 351/206; 351/205; 351/246; 356/496
(58) Field of Classification Search .............. 351/205, 351/206, 210, 221, 246; 356/450, 477, 479, 356/496, 497
See application file for complete search history.

(56) References Cited

U.S. PATENT DOCUMENTS

| 6,137,585 | A | 10/2000 | Hitzenberger |
| 6,288,784 | B1 | 9/2001 | Hitzenberger |
| 2002/0003607 | A1* | 1/2002 | Toida .................. 351/221 |
| 2008/0094637 | A1* | 4/2008 | de Boer et al. .......... 356/479 |

FOREIGN PATENT DOCUMENTS

JP 2002-515593 T 5/2002

* cited by examiner

*Primary Examiner* — Huy K Mai
(74) *Attorney, Agent, or Firm* — Canon USA, Inc. IP Div

(57) ABSTRACT

An optical tomographic imaging method is provided in which light from a light source is split into a measuring beam and a reference beam, the measuring beam being moved by a scanning optical system and guided to an object to be examined, the reference beam being guided to a reference mirror, and in which a tomogram of the object is generated from a return beam of the measuring beam reflected or scattered by the object and the reference beam reflected by the reference mirror. The method includes acquiring longitudinal sectional information on the object, calculating depth-position information on the object from the longitudinal sectional information, and acquiring a three-dimensional surface image of the object by controlling a reference-path length defined by the reference mirror and a scanning operation of the scanning optical system in accordance with the depth-position information on the object.

9 Claims, 13 Drawing Sheets

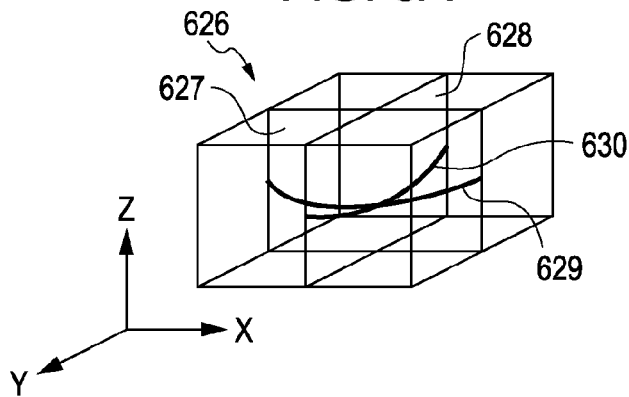
FIG. 6A
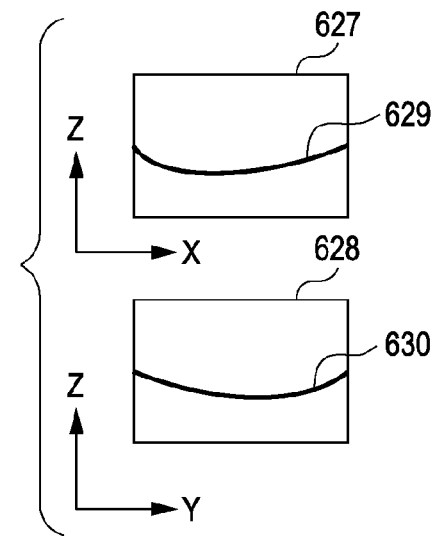
FIG. 6B
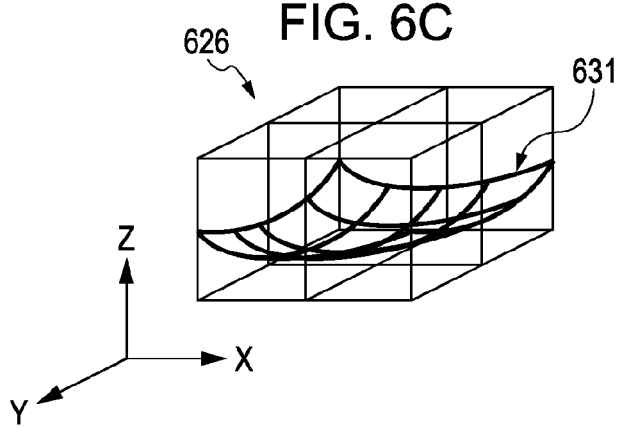
FIG. 6C
FIG. 6D
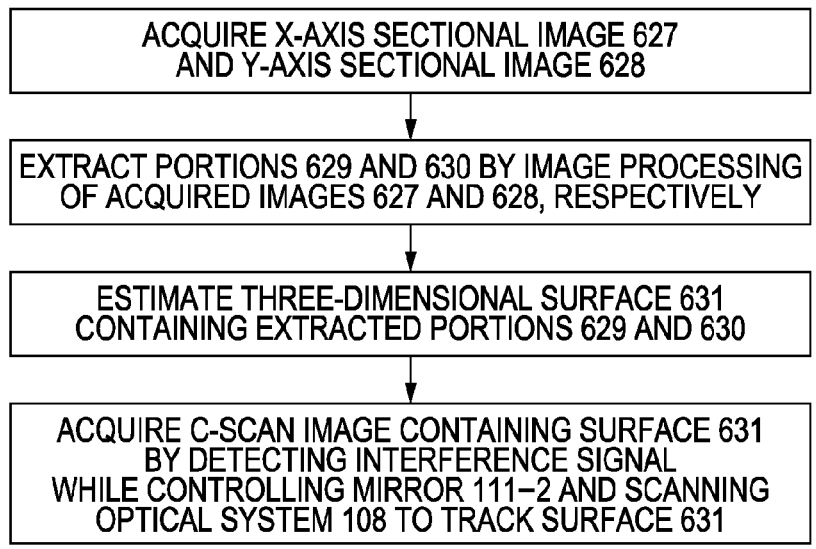

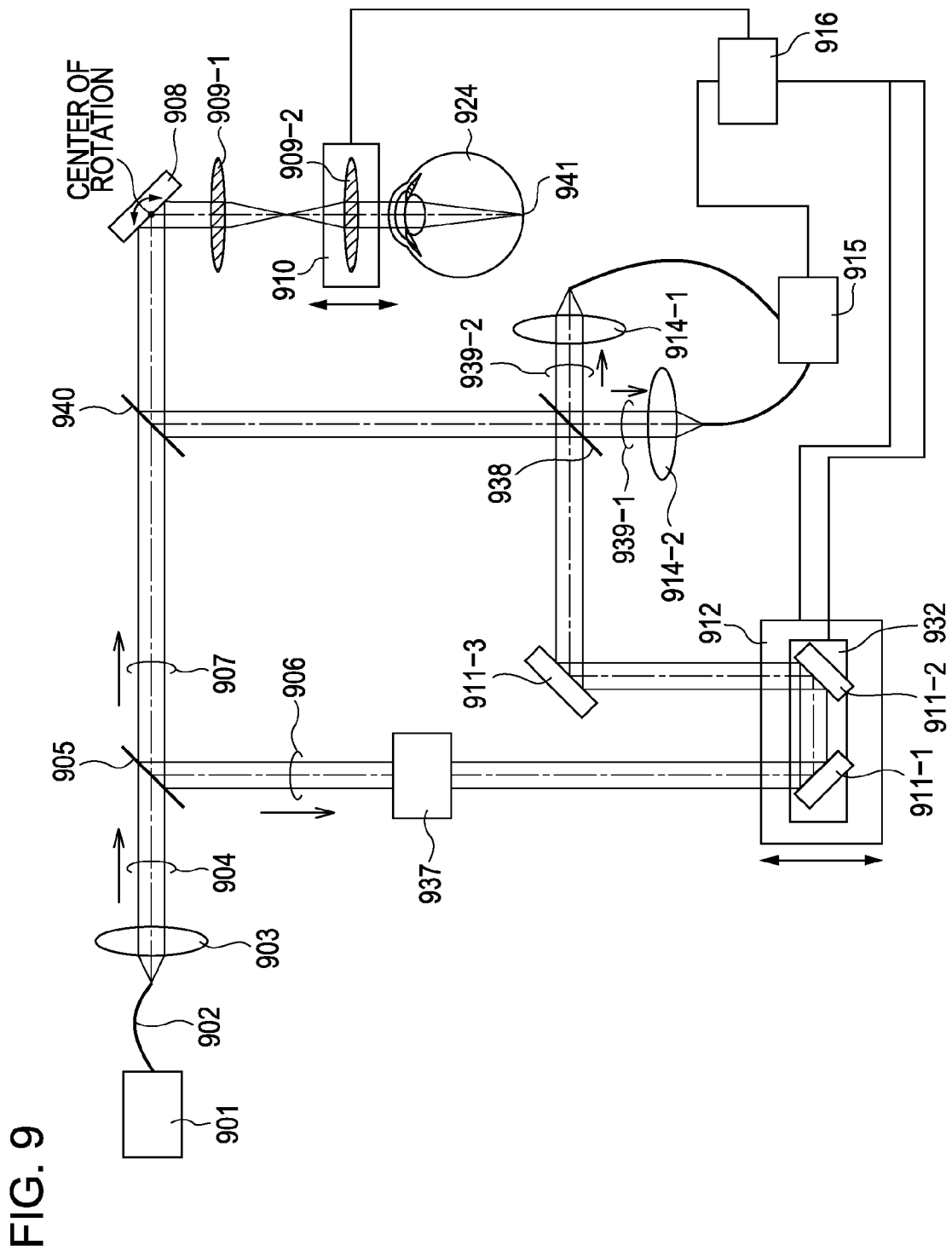

OPTICAL TOMOGRAPHIC IMAGING METHOD AND APPARATUS

BACKGROUND OF THE INVENTION

1. Field of the Invention

The present invention relates to optical tomographic imaging methods and apparatuses, and in particular to an optical tomographic imaging method and apparatus employing optical coherence tomography in the fields of ophthalmic diagnosis and the like.

2. Description of the Related Art

In recent years, imaging apparatuses utilizing interference of low-coherence light have been in practical use.

In particular, an optical tomographic imaging apparatus based on optical coherence tomography (hereinafter abbreviated as OCT) in which multiple-wavelength interference is utilized provides a high-resolution tomogram of a sample. OCT apparatuses have been becoming essential, particularly in the field of ophthalmic diagnosis, for acquisition of a tomogram of the eyeground or a region therearound.

Other than in ophthalmic diagnosis, OCT apparatuses are also used in, for example, tomographic examination of the skin and, by being incorporated into endoscopes and catheters, in tomography of the walls of digestive and circulatory organs.

Such OCT methods include a time-domain OCT (TD-OCT) method. Examples are disclosed in U.S. Pat. No. 5,321,501 and PCT Japanese Translation Patent Publication No. 2002-515593 (pages 9 to 19 and FIGS. 1 and 2 therein).

A TD-OCT method will now be described.

FIG. 2 is a diagram of a known TD-OCT apparatus.

Referring to FIG. 2, light emitted from a light source 2101 travels through an optical fiber 2102, is guided to a collimator 2103, and is output as a collimated beam 2104 from the collimator 2103.

The collimated beam 2104 is split into a reference beam 2106 and a signal beam 2107 by a beam splitter 2105.

The reference beam 2106 is reflected by a movable reference mirror 2111-2.

The movable reference mirror 2111-2 is moved by a reference mirror stage 2112 mechanically movable in a one-dimensional direction, thereby controlling the measurement point in an object 2117 to be examined. The measurement point is controlled in an optical-axis direction of the signal beam 2107 entering the object 2117.

The signal beam 2107 is directed by a scanning optical system 2108 in such a direction as to travel through eyepiece members 2109-1 to 2109-3, thereby entering the object 2117.

The beam that has entered the object 2117 is reflected by layers in the object 2117 and returns to the beam splitter 2105.

The scanning optical system 2108 performs scanning by moving the signal beam 2107 entering the object 2117 in specific directions.

The reflections from the movable reference mirror 2111-2 and the object 2117 enter the beam splitter 2105 and interfere with each other, producing an interference beam 2113. The interference beam 2113 is condensed by a collimator 2114 and is guided to a detector 2115.

The condensed beam is detected as a signal by the detector 2115 and is imaged by a control computer 2116.

The control computer 2116 controls the eyepiece member 2109-2 by moving a focusing stage 2110 so as to adjust the focus of the beam incident on the object 2117.

The control computer 2116 also controls the reference mirror stage 2112, thereby being capable of identifying, with reference to the detected interference signal and the position of the reference mirror stage 2112, the depth in the object 2117 indicated by the detected signal.

Thus, in the TD-OCT method, image data can be generated from pieces of data representing the intensity of the interference beam, the pieces of data being successively acquired by performing scanning with the scanning optical system 2108 while controlling the movable reference mirror 2111-2.

For example, in A-scan (scanning in the optical-axis direction of a beam entering an object, i.e., the depth direction of an object), the signal beam 2107 entering the object 2117 is moved by the scanning optical system 2108 in one direction (for example, the X-axis direction) within a plane in the object 2117.

Thus, pieces of one-dimensional A-scan data can be successively acquired.

From such successively acquired images, a B-scan image (a two-dimensional image of a longitudinal section) can be acquired.

If the signal beam 2107 is moved in two directions (for example, the X- and Y-axis directions) within the foregoing plane without moving the reference mirror stage 2112, a C-scan image (a two-dimensional image of a transverse section) can be acquired.

If the signal beam 2107 is moved in two directions (for example, the X- and Y-axis directions) within the foregoing plane while the reference mirror stage 2112 is controlled, a three-dimensional image can be acquired.

Here, A-scan, B-scan, and C-scan mentioned above will be described with reference to FIG. 3.

A signal beam 3207 is made to enter an object 3217 to be examined, as shown in FIG. 3.

The signal beam 3207 is made to enter the object 3217 in the Z-axis direction in FIG. 3. Therefore, in A-scan, information on a structure extending along an axis 3218 in the object 3217 is acquired.

If, in FIG. 3, the signal beam 3207 is moved in the X-axis direction while scanning in the Z-axis direction is performed, information on a plane 3219 is acquired.

The plane 3219 is a longitudinal sectional image. A scanning method providing such an image is referred to as B-scan.

If scanning is performed in the X- and Y-axis directions but not in the Z-axis direction, information on a plane 3220 is acquired.

The plane 3220 is a transverse image of a layer in the object 3217. A scanning method providing such an image is referred to as C-scan.

There is another OCT method, a spectral-domain OCT (SD-OCT) method. An example is disclosed in "Handbook of Optical Coherence Tomography" (2006; FIGS. 2 and 3 in pages 145 and 149, and FIG. 1 in page 338).

The SD-OCT method will now be described.

FIG. 4 is a diagram of a known SD-OCT apparatus.

The SD-OCT apparatus shown in FIG. 4 differs from the TD-OCT apparatus shown in FIG. 2 in the following aspects.

The SD-OCT apparatus includes a fixed reference mirror 4323 instead of the movable reference mirror 2111-2, spectroscope members 4321-1 and 4321-2 including a diffraction grating, and a spectroscopic detector 4322, such as a line sensor, instead of the detector 2115.

In the SD-OCT apparatus, a spectrum acquired by the spectroscope members 4321-1 and 4321 is detected by the spectroscopic detector 4322.

In the SD-OCT apparatus, the detected spectrum, which is composed of pieces of information on the intensity of an interference beam 4313 expressed with respect to an axis representing the wavelength, is subjected to a Fourier transform into information expressed with respect to an axis representing the position of the scanned plane, whereby image data is acquired collectively in terms of time.

In the SD-OCT apparatus, since image data in the depth direction of an object 4307 is collectively acquired, measurement speed can be increased compared with the case in the TD-OCT apparatus in which scanning in the depth direction is performed successively in terms of time.

It is known that SD-OCT apparatuses can acquire B-scan images and three-dimensional images at higher speeds than in TD-OCT apparatuses. Instead, it is pointed out that there is a difficulty in increasing the transverse resolution in SD-OCT apparatuses.

This is because, in SD-OCT apparatuses, the measurement range of an object in the depth direction thereof is inversely proportional to the transverse resolution. Therefore, to acquire information on a longitudinal section having a sufficient area, the transverse resolution needs to be reduced.

In recent years, there has been a demand for OCT apparatuses having increased image resolutions.

There has also been a strong demand for capability of concentrated examination of an arbitrary layer in an object, and accordingly a demand for apparatuses capable of taking C-scan images with high resolutions and at high speeds.

The known TD-OCT and SD-OCT apparatuses described above, however, have the following problems in satisfying such recent demands.

For example, the known TD-OCT apparatus described above can acquire a two-dimensional image of a transverse section by C-scan in which the signal beam 2107 is moved in two directions (for example, the X- and Y-axis directions) within a plane without moving the reference mirror stage 2112.

In this operation of the TD-OCT apparatus, only a signal from a specific depth defined by the movable reference mirror 2111-2 is acquired. Therefore, by focusing the signal beam 2107 on the specific depth, a transverse-sectional image with a very high resolution can be acquired.

In this case, however, since the signal beam 2107 is moved with the movable reference mirror 2111-2 fixed, only a two-dimensional image of a transverse-sectional image at a constant depth is acquired.

Therefore, in a case where a desired object to be examined is a curved layer, such as an internal structure of a retina, only fragmental transverse-sectional images of the desired layer are acquired.

Another method can be considered in which three-dimensional information is generated from successively acquired B-scan images, and a surface of an arbitrary desired layer is extracted from the three-dimensional information. Such a method, however, requires a long time for acquisition of three-dimensional information. Besides, if the object moves during acquisition of such information, the resulting image may blur and clear information may not be acquired.

In addition, to generate three-dimensional image information, high-load processing needs to be performed. This leads to a problem of a very long processing time.

On the other hand, in the SD-OCT apparatus, information in the depth direction over a wide range can be acquired collectively, whereas it is difficult to increase transverse resolution.

If the transverse resolution of the SD-OCT apparatus is increased, the longitudinal dimension of a range in which information can be collectively acquired is also reduced, and the speed of information acquisition is also reduced to a level equal to or less than that in the TD-OCT apparatus.

Moreover, to acquire information on an arbitrary surface, three-dimensional information first needs to be generated from a plurality of B-scan images, and then an image of the surface needs to be extracted, as in the TD-OCT apparatus.

Such acquisition of high-resolution three-dimensional information also requires a very long time. Besides, if the object to be examined moves, the resulting image may blur.

In addition, it takes a very long processing time, as in the TD-OCT apparatus.

SUMMARY OF THE INVENTION

In light of the above, the present invention provides an optical tomographic imaging method and apparatus enabling acquisition of a surface image of an arbitrary layer in an object to be examined and acquisition of such a surface image in a short time even if the layer is curved.

According to a first aspect of the present invention, an optical tomographic imaging method is provided in which light from a light source is split into a measuring beam and a reference beam, the measuring beam being moved by a scanning optical system and guided to an object to be examined, the reference beam being guided to a reference mirror, and in which a tomogram of the object is generated from a return beam of the measuring beam reflected or scattered by the object and the reference beam reflected by the reference mirror. The method includes acquiring longitudinal sectional information on the object, calculating depth-position information on the object from the longitudinal sectional information, and acquiring a three-dimensional surface image of the object by controlling a reference-path length defined by the reference mirror and a scanning operation of the scanning optical system in accordance with the depth-position information on the object.

According to a second aspect of the present invention, an optical tomographic imaging apparatus is provided in which light from a light source is split into a measuring beam and a reference beam, the measuring beam being guided to an object to be examined, the reference beam being guided to a reference mirror, and in which a tomogram of the object is generated from a return beam of the measuring beam reflected or scattered by the object and the reference beam reflected by the reference mirror. The apparatus includes a scanning optical system capable of moving the measuring beam in one-dimensional and two-dimensional manners, a reference-path-length adjuster provided to the reference mirror and configured to adjust an optical-path length of the reference beam, and a control unit configured to control the reference-path-length adjuster and the scanning optical system so that a three-dimensional surface image of the object is acquired in accordance with depth-position information on the object estimated in advance.

Further features of the present invention will become apparent from the following description of exemplary embodiments with reference to the attached drawings.

BRIEF DESCRIPTION OF THE DRAWINGS

FIGS. 6A to 6D are diagrams for describing steps of estimating a three-dimensional surface according to the first embodiment of the present invention.

FIG. 9 is a diagram for describing a TD-OCT apparatus and steps of a tomographic imaging method in Example 1 of the present invention.

DESCRIPTION OF THE EMBODIMENTS

Exemplary optical tomographic imaging methods and apparatuses according to embodiments of the present invention will now be described.

While the present invention is suitably applied to the field of tomographic imaging of the retina of an eye, the present invention is not limited thereto.

For example, the present invention may also be applied to biomedical fields of endoscopy, skin examination, and the like, and to industrial fields of product quality control, product diagnosis, product inspection, and the like.

First Embodiment

A first embodiment of the present invention will now be described. The first embodiment concerns a TD-OCT-based optical tomographic imaging method and apparatus.

According to a first exemplary embodiment of the present invention, an optical tomographic imaging method includes the following steps (1) to (4): (1) acquiring, as a first preliminary image, a two-dimensional image of an object to be examined, the image extending in an optical-axis direction in which light enters the object; (2) acquiring, as a second preliminary image, another two-dimensional image of the object, the image extending in the optical-axis direction and being substantially orthogonal to the two-dimensional image acquired in step (1); (3) calculating depth-position information on a desired layer from the image acquired in step (1) and the image acquired in step (2); and (4) acquiring a surface image of the desired layer by moving the light entering the object while controlling a reference mirror in accordance with the depth-position information.

An optical tomographic imaging apparatus and details of the above steps according to the first embodiment will now be described.

Figure 1:
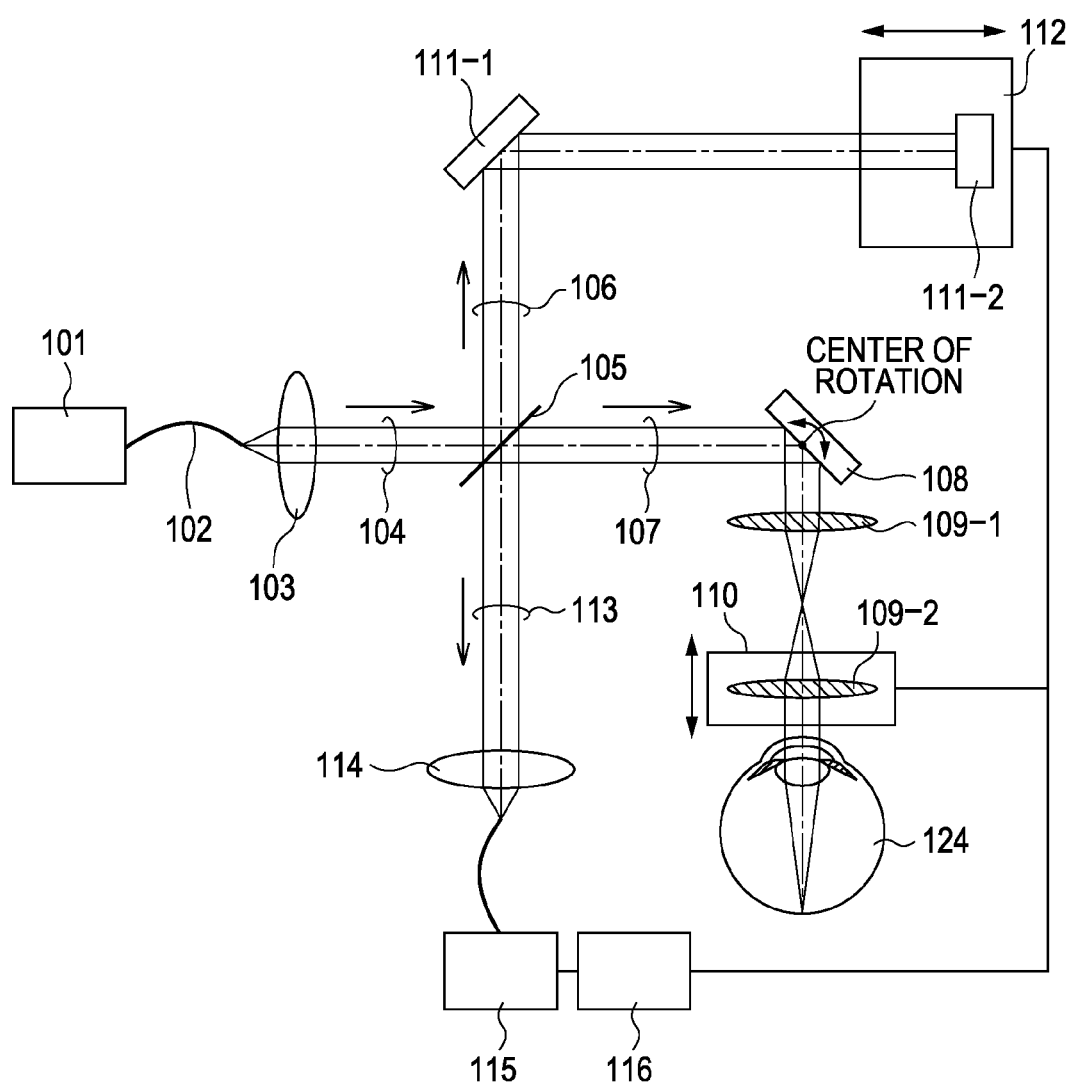
FIG. 1 is a diagram for describing a TD-OCT apparatus and steps of a tomographic imaging method according to a first embodiment of the present invention.
Figure 2:
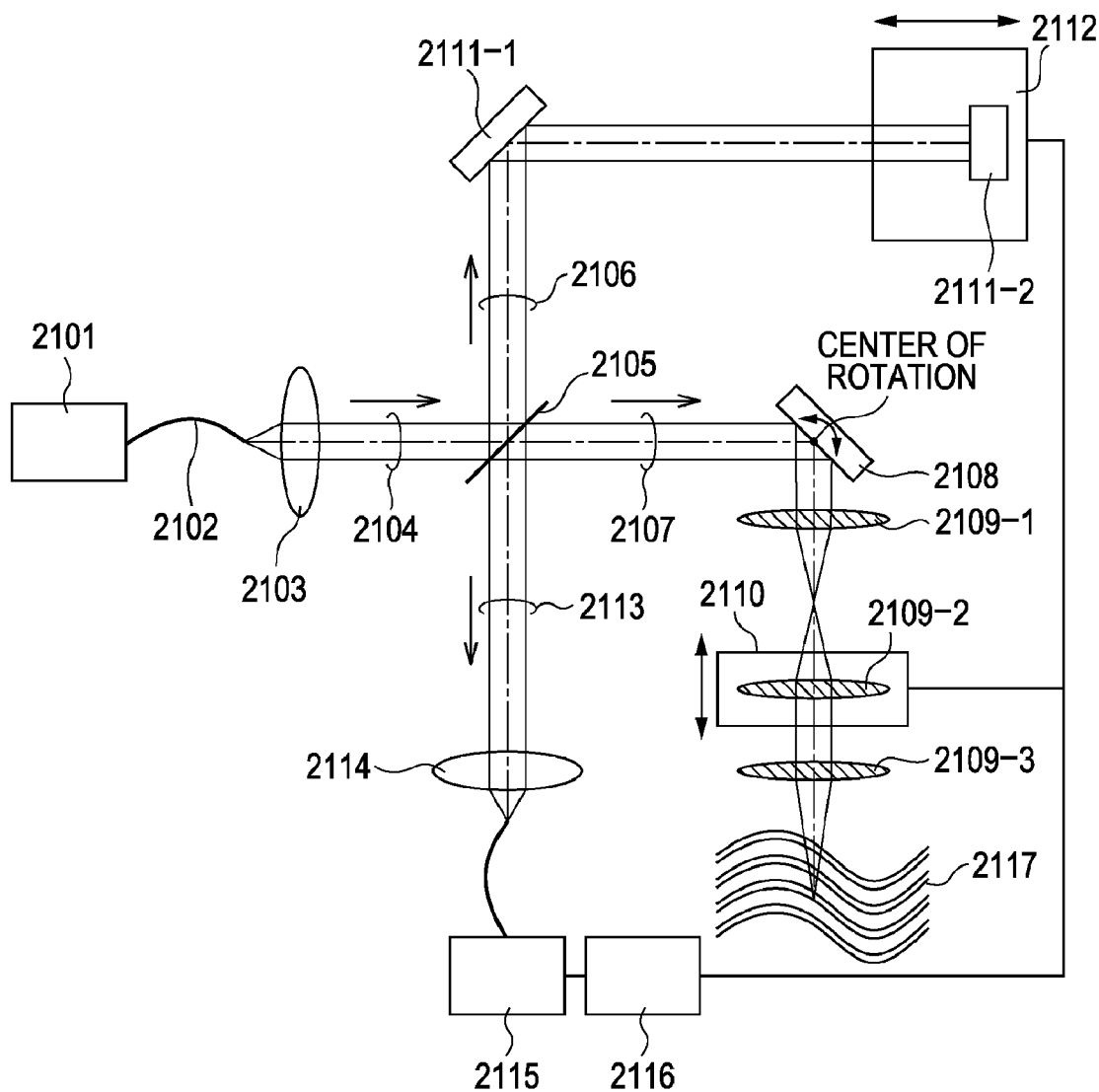
FIG. 2 is a diagram of a known TD-OCT apparatus.
Figure 3:
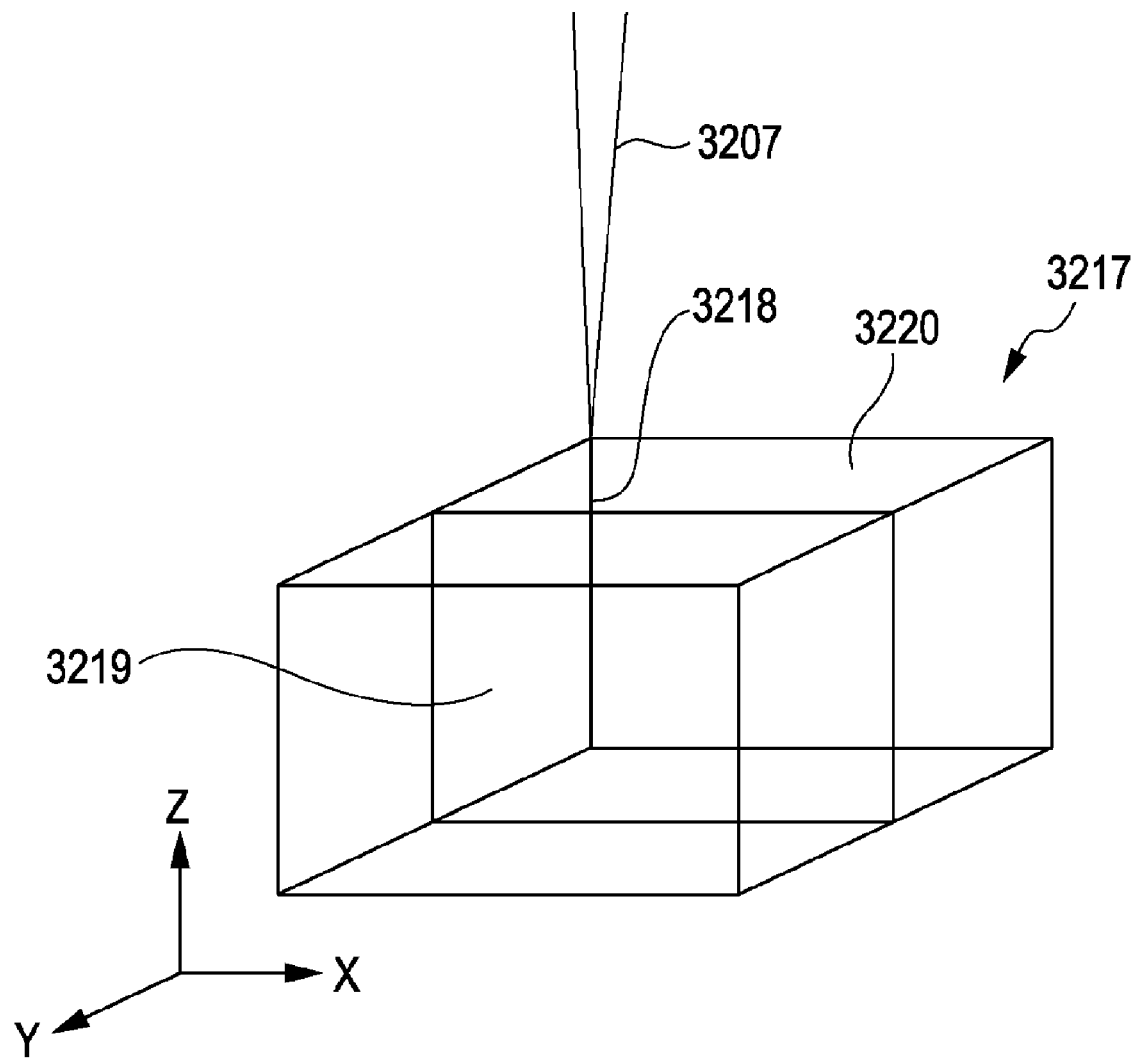
FIG. 3 is a diagram for describing A-scan, B-scan, and C-scan performed in the known TD-OCT apparatus.
Figure 4:
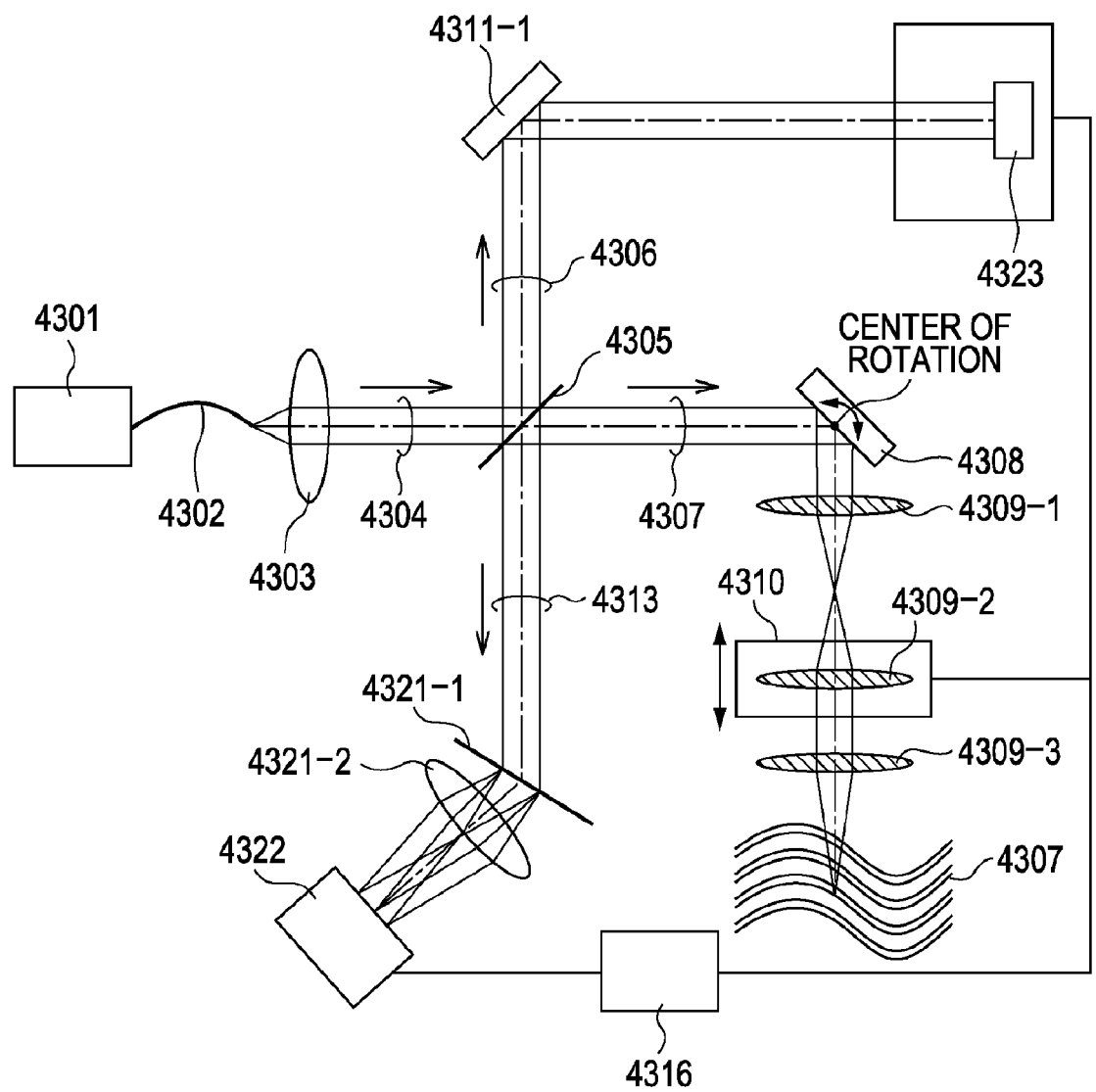
FIG. 4 is a diagram of a known SD-OCT apparatus.

FIG. 1 is a diagram for describing a TD-OCT apparatus and the steps of the tomographic imaging method according to the first embodiment.

FIG. 1 shows a light source 101, an optical fiber 102, a collimator 103, a collimated beam 104, a beam splitter 105, a reference beam 106, a signal beam 107, a scanning optical system 108, eyepiece members 109-1 and 109-2, a focusing stage 110, reference mirrors 111-1 and 111-2, a reference mirror stage 112, an interference beam 113, a collimator 114, a photodetector 115, an OCT processing unit 116, and an object (eye) 124 to be examined.

In the TD-OCT apparatus of the first embodiment, light from the light source 101 is split into the signal beam 107, i.e., a measuring beam, and the reference beam 106, the signal beam 107 being moved by the scanning optical system 108 and guided to the object 124, the reference beam 106 being guided to the reference mirrors 111.

A tomogram of the object 124 is generated from a return beam of the signal beam 107 reflected or scattered by the object 124 and the reference beam 106 reflected by the reference mirrors 111.

The light source 101 is, for example, a low-coherence light source or a superluminescent diode (SLD). The wavelength of the light source 101 is not particularly limited to but is within 400 nm to 2 μm. For imaging of the eyeground, wavelengths of about 800 to 1500 nm are suitable.

The wavelength width for realizing OCT can be set to, for example, 1 pm or larger, specifically, 10 pm or larger, or more specifically, 30 pm or larger.

The light source 101 may alternatively be an ultrashort-pulse laser such as a titanium-sapphire laser. Light emitted from the light source 101 travels through the optical fiber 102 and is collimated by the collimator 103, thereby being output as the collimated beam 104.

The collimated beam 104 is split into the signal beam 107 (a beam traveling toward the object 124) and the reference beam 106 (a beam traveling toward the reference mirrors 111) by the beam splitter 105.

The signal beam 107 is moved by the scanning optical system 108 in one-dimensional and two-dimensional manners. A galvanoscanner can be employed as the scanning optical system 108. The scanning optical system 108 performs one-dimensional scanning for B-scan of the eyeground, and two-dimensional scanning for C-scan and acquisition of a three-dimensional image.

The signal beam 107 moved as aforementioned is adjusted by the eyepiece members 109-1 and 109-2 in accordance with the refraction of the object 124, i.e., the eye, and is applied to the object 124.

For example, the effect of refraction can be adjusted by moving the eyepiece member 109-2 along the optical axis.

The signal beam 107 applied to the eye is reflected and scattered by layers in the retina and returns along substantially the same path to the beam splitter 105.

Meanwhile, the reference beam 106 is reflected by the reference mirrors 111-1 and 111-2 and returns to the beam splitter 105.

The reference mirror 111-2 is controllable with the reference mirror stage 112. The reference mirror stage 112 moves the reference mirror 111-2 in the optical-axis direction, whereby the length of the optical path of the reference beam 106 (hereinafter referred to as the reference-path length) is increased and decreased.

In the TD-OCT apparatus of the first embodiment, the OCT processing unit 116, which is a computer system, controls the entire operation of the apparatus, including the scanning operation of the scanning optical system 108 and the operations of other components such as the focusing stage 110 and the reference mirror stage 112.

The signal beam 107 and the reference beam 106 that have returned to the beam splitter 105 interfere with each other, are transmitted through the collimator 114, and are converted into an electrical signal by the photodetector 115.

In the TD-OCT apparatus of the first embodiment, a signal from a specific depth in the object 124 can be solely detected by causing only rays of the signal beam 107 that have traveled the same length as the reference-path length defined by the position of the reference mirror 111-2 to interfere with the reference beam 106.

The behavior of the signal beam in the eye will now be described.

Figure 5A:
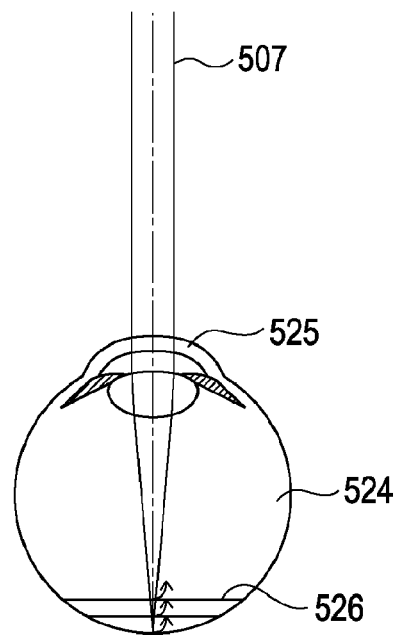
FIGS. 5A and 5B are diagrams for describing the optical path of an exemplary TD-OCT apparatus according to the first embodiment of the present invention in a case where the apparatus is used for eye measurement.
Figure 5B:
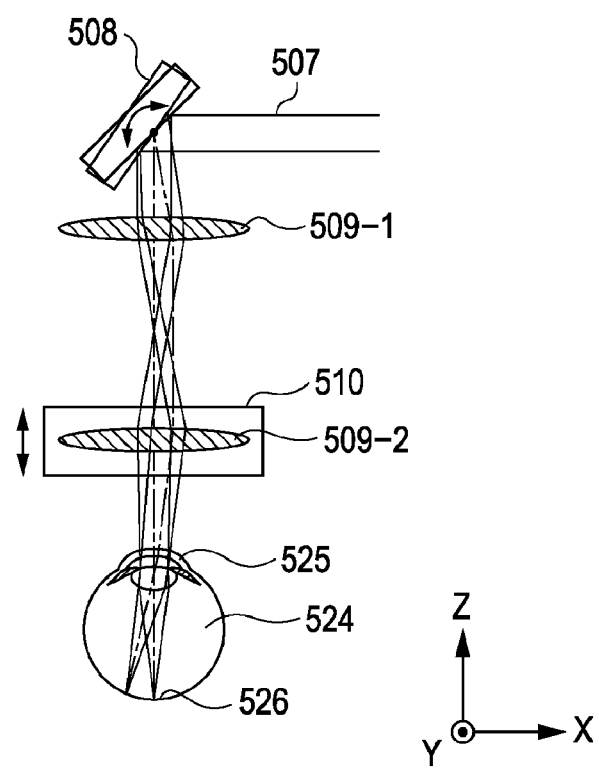

FIGS. 5A and 5B are diagrams for describing the optical path in an exemplary TD-OCT apparatus according to the first embodiment in a case where the apparatus is used for eye measurement.

FIG. 5A shows the optical path of a signal beam 507 in an eye 524.

The signal beam 507 is applied through a cornea 525 to the interior of the eye 524.

The signal beam 507, which is a substantially collimated beam, is focused on a retina 526 because of the effect of refraction caused by the cornea 525 and so forth.

The signal beam 507 is reflected and scattered by layers in the retina 526 of the eye 524, returns along the same path, and is detected as an interference signal.

With a reference mirror being at a specific position, only the signal beam 507 from a specific layer interferes with a reference beam. Therefore, signals from different layers are detected as different signals.

FIG. 5B shows the optical path of the signal beam 507 in the eye 524 in a case where scanning is performed by a scanning optical system 508.

If the scanning optical system 508 is moved, the incident angle of the signal beam 507 at the cornea 525 changes, whereby the focal position on the retina 526 changes.

If the reference mirror and the scanning optical system 508 are moved during detection of the interference beam, a B-scan image of the retina 526 is acquired.

If the scanning optical system 508 is moved with the reference mirror being fixed at a specific position during detection of the interference beam, a C-scan image, i.e., an image of a transverse section, defined by rays of the signal beam 507 of a constant length is acquired.

The aforementioned steps of acquiring a tomogram with the TD-OCT apparatus according to the first embodiment will now be described.

First, in step (1), a two-dimensional image extending in the optical-axis direction in which the light enters the object is acquired.

Specifically, the scanning optical system 108 is moved in a one-dimensional manner while the reference mirror 111-2 is controlled, whereby a B-scan image, i.e., a longitudinal sectional image, of the eyeground of the object 124 is acquired.

The B-scan image is treated as a first preliminary image. The B-scan image extends in, for example, the X-axis direction in FIG. 5B.

In step (2), another two-dimensional image that is substantially orthogonal to the two-dimensional image acquired in step (1) is acquired.

Specifically, the scanning optical system 108 is moved in a one-dimensional manner in a direction substantially orthogonal to the direction in step (1) while the reference mirror 111-2 is controlled as in step (1), whereby another B-scan image orthogonal to the first preliminary image is acquired as the second preliminary image.

The second preliminary image is a B-scan image extending in the Y-axis direction in FIG. 5B.

In step (3), depth-position information on a desired layer is calculated from the first preliminary image acquired in step (1) and the second preliminary image acquired in step (2), i.e., longitudinal sectional information. The calculation is performed as follows.

Three-dimensional position information on a desired layer is calculated from the first and second preliminary images.

FIG. 6A shows an exemplary region 626 containing a desired layer.

An X-axis sectional image 627 is acquired as a first preliminary image. The first preliminary image 627 contains a portion 629 of the desired layer.

Subsequently, a Y-axis sectional image 628 is acquired as a second preliminary image. Similar to the first preliminary image 627, the second preliminary image 628 contains a portion 630 of the desired layer.

Position information on the portion 629 is extracted from the first preliminary image 627 by image processing. Likewise, position information on the portion 630 is extracted from the second preliminary image 628 by image processing.

With reference to the position information, a three-dimensional surface 631, shown in FIG. 6C, containing the portions 629 and 630 is estimated.

A specific exemplary method of estimating the three-dimensional surface 631 will now be described.

The position information on the portion 629 is extracted from the first preliminary image 627 and is fitted to an appropriate function.

For example, the position information is fitted to a function of $Z=X^2$, with the X-axis-direction center being defined as the origin.

Likewise, the position information on the portion 630 is extracted from the second preliminary image 628 and is fitted to a function of $Z=Y^2$. Combining the two functions results in a function of $Z=X^2+Y^2$, which expresses positional information on the three-dimensional surface 631.

In step (4), the light entering the object is moved while the reference mirror is controlled in accordance with the depth-position information, whereby a three-dimensional surface image of the desired layer is acquired as follows.

In accordance with the position information on the three-dimensional surface, i.e., the depth-position information calculated as above, the reference mirror 111-2 and the scanning optical system 108 are controlled, whereby a C-scan image containing the three-dimensional surface 631 is acquired.

FIG. 6D is a flowchart of a process for acquiring an image through the steps described above using the TD-OCT apparatus of the first embodiment.

The reference mirror 111-2 can be controlled by, as shown in FIG. 1, the reference mirror stage 112 for the purposes of both adjustment of the reference-path length when a B-scan image is acquired and tracking of the three-dimensional surface 631.

The reference mirror stage 112, i.e., a reference-path-length adjuster, can include a stage capable of coarse adjustment performed in acquiring position information and a stage capable of fine adjustment performed in acquiring a three-dimensional surface image.

Figure 7:
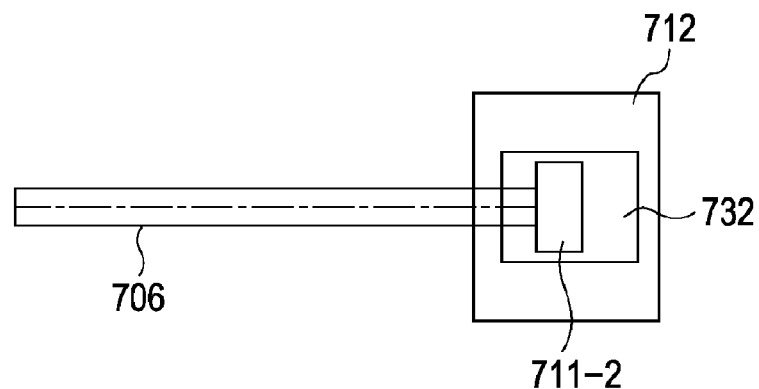
FIG. 7 is a diagram of an exemplary reference-path-length adjuster included in the TD-OCT apparatus according to the first embodiment of the present invention.

FIG. 7 shows an exemplary reference-path-length adjuster. The adjuster includes a stage 712 intended for acquisition of a B-scan image and being movable within a wide range, a stage 732 provided on the stage 712 and capable of fine and quick adjustment, and a reference mirror 711-2 provided on the stage 732. In this case, it is desirable that the stage 712 be configured as a linear motor stage or the like, and the stage 732 be configured as a voice coil motor stage or the like that is movable at a high speed.

In the first embodiment, a three-dimensional surface image can alternatively be acquired by, instead of controlling the reference-path length determined by the reference mirror, controlling the point in the object at which the measuring beam guided to the object is incident.

Control of the plane along which information is to be acquired can be performed by, other than by controlling the reference mirror, controlling the position of the entrance pupil. This control method will now be described with reference to FIG. 8.

Figure 8:
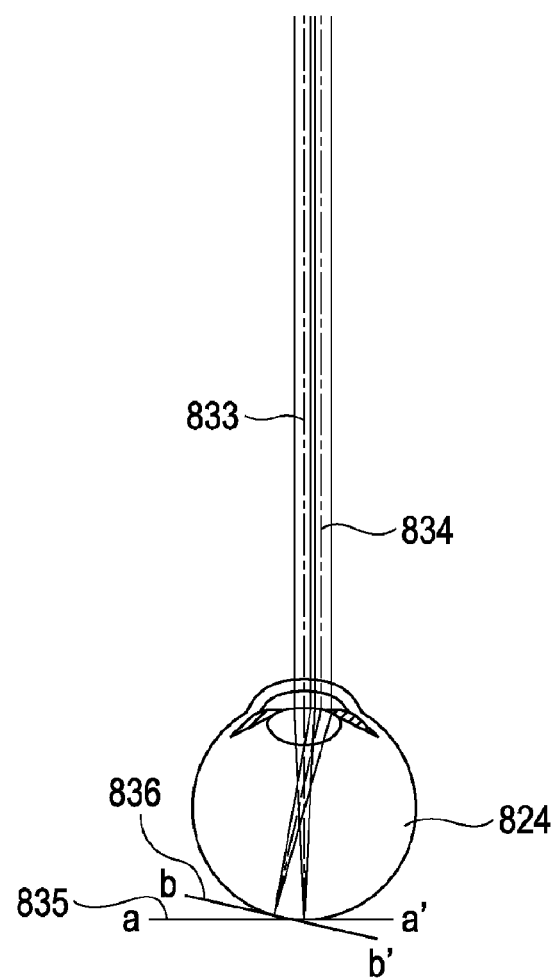
FIG. 8 is a diagram for describing a method of controlling the position of the entrance pupil, instead of controlling a reference mirror, in controlling a plane along which information is to be acquired in the first embodiment of the present invention.

Referring to FIG. 8, if a beam 833 entering an eye 824 through the center of the cornea is moved by a scanning optical system, an image of a plane 835 containing the line a-a' that is parallel to the retina is acquired.

In contrast, if a beam 834 that is parallel to the beam 833 but does not pass through the center of the cornea is moved by the scanning optical system, an image of a plane 836 containing the line b-b' is acquired.

Thus, by changing the position of the pupil through which the signal beam passes, the inclination of a plane along which information is to be acquired can be controlled.

By controlling the position of the pupil in accordance with the three-dimensional surface 631, the plane along which information is to be acquired can be changed successively, whereby a C-scan image representing the three-dimensional surface 631 can be acquired.

The position of the pupil can be controlled by controlling the position of an object to be examined. Alternatively, the position of the pupil may be controlled by controlling the position optically conjugate to the pupil of the object, or by controlling the position of the collimator intended for detection.

While the first embodiment concerns a TD-OCT apparatus, the present invention is not limited thereto.

For example, the present invention may also be applied to a case where a tomogram is acquired by using a frequency-domain OCT (FD-OCT) apparatus that does not require mechanical scanning.

Second Embodiment

An optical tomographic imaging method according to a second embodiment of the present invention will now be described in which a TD-OCT apparatus is used.

According to another aspect of the present invention, an optical tomographic imaging method according to a second embodiment includes the following steps (1) to (4): (1) acquiring, as a first preliminary image, a two-dimensional image of an object to be examined, the image extending in an optical-axis direction in which light enters the object; (2) acquiring, as second and subsequent preliminary images, a plurality of two-dimensional images of the object, the images extending in the optical-axis direction and being substantially parallel to the two-dimensional image acquired in step (1); (3) calculating depth-position information on a desired layer from the image acquired in step (1) and the images acquired in step (2); and (4) acquiring a surface image of the desired layer by moving the light entering the object while controlling a reference mirror in accordance with the depth-position information.

The second embodiment is basically the same as the first embodiment, except that, in step (2), a plurality of longitudinal sectional images substantially parallel to the first preliminary image are acquired as the second and subsequent preliminary images.

In step (2), acquiring as many longitudinal sectional images as possible is effective for improving the accuracy in the estimation of the three-dimensional surface performed in step (3). Nevertheless, the more the number of images to be acquired, the longer the time required for acquiring such images. Therefore, the number of images to be acquired needs to be determined considering the speed of image acquisition.

An exemplary method of calculating the three-dimensional surface according to the second embodiment will now be described.

As in the first embodiment, position information on the portion of the desired layer is extracted from the first preliminary image and is fitted to an appropriate function, that is, a function of $Z=X^2$ is obtained.

Subsequently, from the second preliminary image parallel to the first preliminary image, a function of $Z=X^2+1$ (where $Y=1$) is obtained.

Likewise, from the third and fourth preliminary images, functions of $Z=X^2+2$ (where $Y=2$) and $Z=X^2+3$ (where $Y=3$) are obtained, respectively.

Considering the foregoing functions, it is understood that position information representing the surface of the desired layer can be expressed as $Z=X^2+Y$.

Moreover, if images that are substantially orthogonal to the first preliminary image and images that are substantially parallel to the first preliminary image are both acquired in step (2), the accuracy in the three-dimensional position information is further improved.

Third Embodiment

An optical tomographic imaging method according to a third embodiment of the present invention will now be described in which a TD-OCT apparatus utilizing a plurality of pieces of one-dimensional information is used.

According to an aspect of the present invention, an optical tomographic imaging method according to a third embodiment includes the following steps (1) to (3): (1) acquiring, as a first preliminary image, a plurality of one-dimensional images of an object to be examined, the images extending in an optical-axis direction in which light enters the object; (2) calculating depth-position information on a desired layer from the images acquired in step (1); and (3) acquiring a surface image of the desired layer by moving the light entering the object while controlling a reference mirror in accordance with the depth-position information.

In step (1), a plurality of A-scan images (pieces of one-dimensional information) are acquired. In step (2), position information on the desired layer is calculated from the plurality of A-scan images.

In the third embodiment, acquisition of the A-scan images in step (1) does not require mechanical scanning. Therefore, an FD-OCT apparatus capable of high-speed acquisition of an A-scan image is desirably used.

Steps (2) and (3) are the same as steps (3) and (4) in the first embodiment.

EXAMPLES

Examples of the present invention will now be described.

Example 1

Example 1 will first be described in which the TD-OCT apparatus according to any of the embodiments of the present invention is applied to eyeground examination. In Example 1, a surface image of the pigmented layer in the retina is acquired. The present invention is not limited to such eyeground examination.

FIG. 9 is a diagram for describing a TD-OCT apparatus and steps of a tomographic imaging method in Example 1.

In Example 1, light emitted from a light source 901 is guided by a single-mode optical fiber 902. The light output from the end of the optical fiber 902 is collimated into a collimated beam 904 by a collimator 903. The collimated beam 904 is split into a reference beam 906 and a signal beam 907 by a beam splitter 905.

The light source 901 is an SLD having a center wavelength of 840 nm and a wavelength width of about 50 nm.

The reference beam 906 is shifted by a frequency shifter 937 such that the optical frequency thereof is shifted by $\Delta f$, is subsequently reflected by reference mirrors 911-1 and 911-2, and is further directed by a reflecting mirror 911-3 toward a combining optical system 938.

The positions of the reference mirrors 911-1 and 911-2 are controlled by mirror position adjusters 912 and 932 such that the reference-path length becomes a specific value.

The mirror position adjuster 912 is a linear motor stage movable with a stroke of 25 mm. The mirror position adjuster 932 is a voice coil motor stage movable with a stroke of 1 mm.

The signal beam 907 first enters a beam guide-splitter 940 and is guided into an examination optical system facing an eye 924, i.e., an object to be examined.

The examination optical system includes the beam guide-splitter 940, a scanning optical system 908, a scanning lens 909-1, and an eyepiece lens 909-2.

The eyepiece lens 909-2 is moved in the optical-axis direction of the beam incident thereon by a focus position adjuster 910. The scanning optical system 908 tilts the chief ray of the signal beam 907 in two directions orthogonal to the optical axis.

Thus, the beam transmitted through the scanning lens 909-1 and the eyepiece lens 909-2 is moved so as to have a variable angle with respect to the pupil (iris) of the eye 924.

Consequently, because of the optical effect of the eye 924, an eyeground-examination target site 941 is scanned within a plane (XY plane) on the eyeground, the plane being perpendicular to the optical axis extending in the depth direction.

Some rays of reflections and backscattered light from the target site 941 return along substantially the same path as the incident path to the target site 941. Such return rays enter the beam guide-splitter 940, and some rays thereof are further guided to the combining optical system 938.

The combining optical system 938 combines the signal beam 907 and the reference beam 906 together and then splits the combined beam into interference beams 939-1 and 939-2 having composite amplitudes, i.e., complex amplitudes, obtained by adding the signal beam 907 and the reference beam 906, the composite amplitudes being out of phase with each other. Some rays of the interference beams 939-1 and 939-2 enter condenser optical systems 914-1 and 914-2, respectively.

The rays of the interference beams 939-1 and 939-2 are optically coupled to respective single-mode optical fibers connecting the condenser optical systems 914-1 and 914-2 to a photoelectric conversion detector 915, whereby components of the rays matching the modes of the respective fibers are selected, propagate inside the fibers, and enter the photoelectric conversion detector 915.

The photoelectric conversion detector 915 converts the rays into electrical signals. The electrical signals are transmitted to an OCT processing unit 916.

Here, the components matching the modes of the fibers each refer to a confocal component that is conjugate to a ray scattered from a point on the target site 941.

The composite amplitudes, i.e., the complex amplitudes, of the interference beams 939-1 and 939-2 obtained by adding the reference beam 906 and the signal beam 907 are each an amplitude of heterodyne interference having a carrier frequency corresponding to a frequency difference $\Delta f$ produced by the frequency shifter 937.

The wave of the heterodyne interference is an oscillation having a frequency $\Delta f$, and the absolute amplitude of the oscillation changes temporally.

The composite amplitudes of the interference beams 939-1 and 939-2 received by the respective condenser optical systems 914-1 and 914-2 have temporal oscillations that are in phase opposition. Thus, by the a TD-OCT method, C-scan images (images each extending within an XY plane intersecting the Z-axis direction, i.e., the depth direction) at focal positions at different depths in the object can be acquired.

The process of acquiring a surface image by the optical tomographic imaging method in Example 1 will now be described.

Figure 10A:
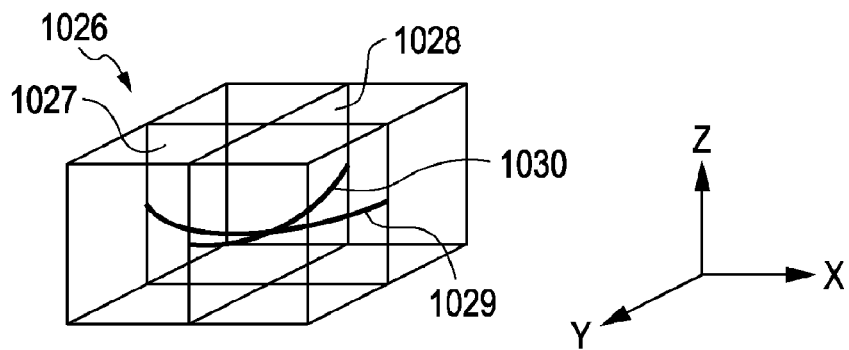
FIGS. 10A to 10C are diagrams for describing steps of estimating a three-dimensional surface in Example 1 of the present invention.
Figure 10B:
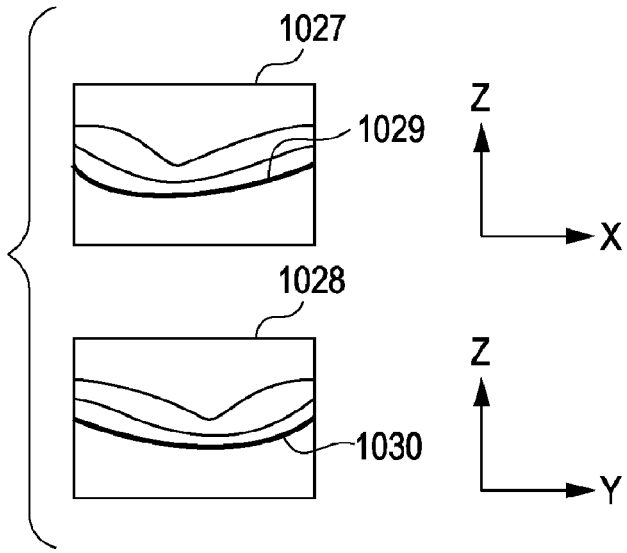
Figure 10C:
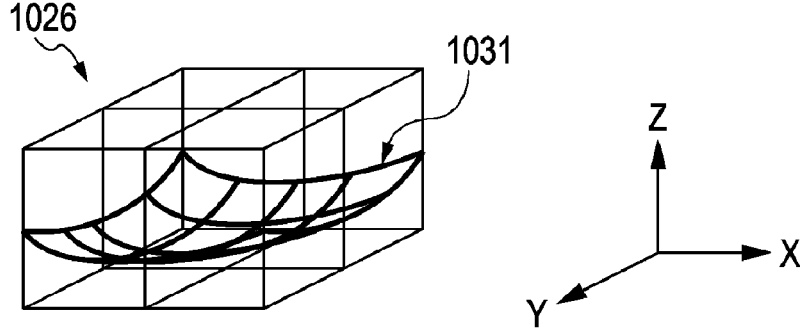

FIGS. 10A to 10C are diagrams for describing steps of estimating a three-dimensional surface in Example 1.

First, a B-scan image of a region 1026 containing a desired layer is acquired.

Specifically, while the mirror position adjuster 912 is moved, the scanning optical system 908 is controlled such that scanning is performed in the X-axis direction in FIG. 10A, whereby a first B-scan image 1027 is acquired.

Subsequently, while the mirror position adjuster 912 is moved, the scanning optical system 908 is controlled such that scanning is performed in the Y-axis direction in FIG. 10A, whereby a second B-scan image 1028 representing a longitudinal section orthogonal to the first B-scan image 1027 is acquired.

The first B-scan image 1027 represents a longitudinal section of the retina and contains a portion 1029 of the pigmented layer, i.e., the desired layer.

Likewise, the second B-scan image 1028 contains a portion 1030 of the pigmented layer, i.e., the desired layer.

The two-dimensional shape of the pigmented layer in the portion 1029 is calculated from the first B-scan image 1027 by image processing.

In general, the pigmented layer has the highest reflectivity in the retina. Therefore, the shape of the pigmented layer can be calculated by, for example, extracting regions having high brightness with respect to the Z-axis direction.

Likewise, the two-dimensional shape of the pigmented layer in the portion 1030 is calculated from the second B-scan image 1028. Subsequently, three-dimensional position information on the pigmented layer is estimated from the calculated two-dimensional shapes that are orthogonal to each other, whereby a surface 1031 representing the pigmented layer is acquired.

Then, while the mirror position adjuster 932, which is a fine-motion stage, is controlled, the scanning optical system 908 is moved such that interference occurs along the surface 1031, whereby a C-scan image of the surface 1031 is acquired. The C-scan image in its entirety represents the surface of the pigmented layer.

Example 2

Example 2, different from Example 1, will now be described in which the TD-OCT apparatus according to any of the embodiments of the present invention is applied to eyeground examination. In Example 2, a surface image of the pigmented layer in retinal cells of an eye to be examined is acquired.

Example 2 is basically the same as Example 1, except that the B-scan images acquired for calculation of three-dimensional information on the pigmented layer are substantially parallel to each other.

In Example 2, a tomogram of the retina is acquired by using the apparatus shown in FIG. 9, as in Example 1.

The process of acquiring a tomogram of the retina will now be described.

Figure 11A:
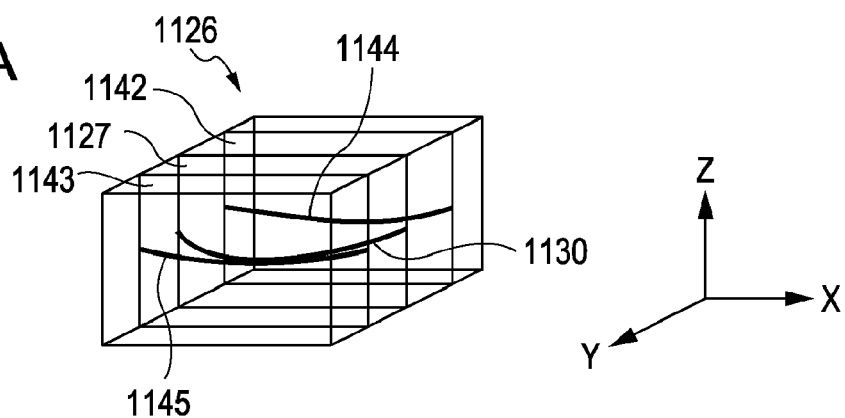
FIGS. 11A to 11C are diagrams for describing steps of estimating a three-dimensional surface in Example 2 of the present invention.
Figure 11B:
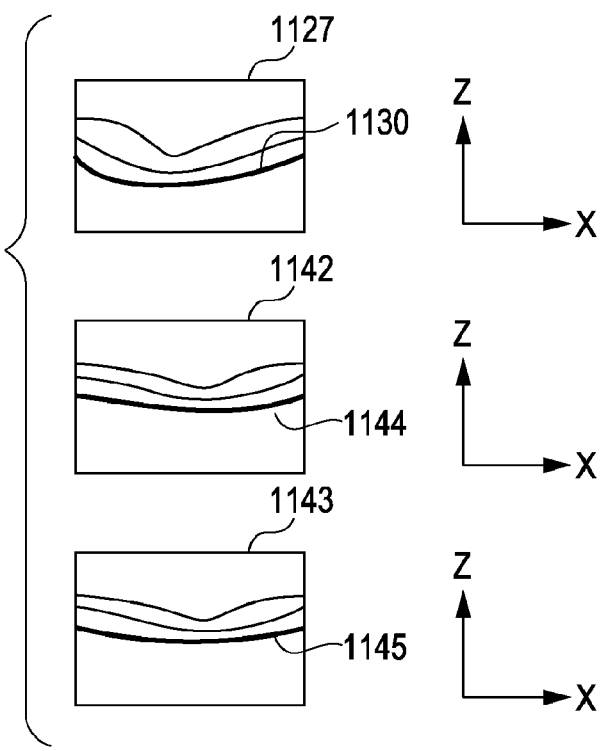
Figure 11C:
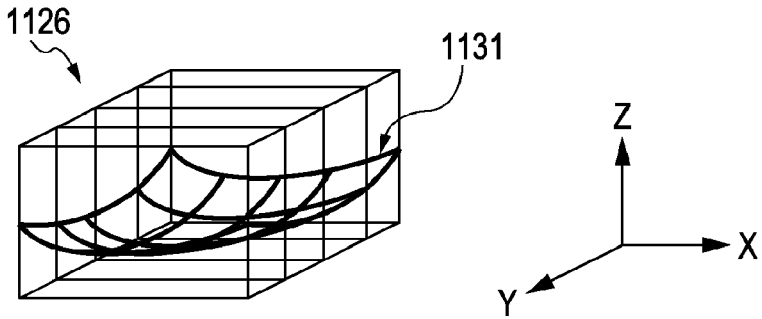

FIGS. 11A to 11C are diagrams for describing steps of estimating a three-dimensional surface in Example 2.

In Example 2, a B-scan image of a region 1126 containing a desired layer is first acquired.

Specifically, while the mirror position adjuster 912 is moved, the scanning optical system 908 is controlled such that scanning is performed in the X-axis direction in FIG. 11A, whereby a first B-scan image 1127 is acquired.

Subsequently, the scanning optical system 908 is moved in the Y-axis direction in FIG. 11A and is fixed at a specific position. Then, while the mirror position adjuster 912 is moved, the scanning optical system 908 is controlled such that scanning is performed in the X-axis direction in FIG. 11A, whereby a second B-scan image 1142 parallel to the first B-scan image 1127 is acquired.

Likewise, the scanning optical system 908 is reversely moved in the Y-axis direction in FIG. 11A and is fixed at a specific position. Then, while the mirror position adjuster 912 is moved, the scanning optical system 908 is controlled such that scanning is performed in the X-axis direction in FIG. 11A, whereby a third B-scan image 1143 parallel to the first B-scan image 1127 is acquired.

Thus, three B-scan images that are substantially parallel to each other are acquired.

The three B-scan images 1127, 1142, and 1143 contain images representing respective portions 1130, 1144, and 1145 of the pigmented layer.

Respective pieces of position information on the portions 1130, 1144, and 1145 are extracted by image analysis.

From the extracted pieces of position information, three-dimensional position information on the pigmented layer, i.e., a surface 1131, is estimated.

In accordance with the estimated position information, a C-scan image of the surface 1131 is acquired, as in Example 1.

Example 3

Example 3, different from Examples 1 and 2, will now be described in which the TD-OCT apparatus according to any of the embodiments of the present invention is applied to eyeground examination. In Example 3, a surface image of the pigmented layer in retinal cells of an eye to be examined is acquired.

In Example 3, three-dimensional information on the pigmented layer is calculated from a plurality of A-scan images.

Such a method can be performed in the same manner as in Example 1. Alternatively, an FD-OCT apparatus capable of high-speed acquisition of an A-scan image may be used.

In Example 3, a tomogram of the retina is acquired by using the TD-OCT apparatus shown in FIG. 9, as in Example 1.

The process of acquiring a tomogram of the retina will now be described.

Figure 12C:
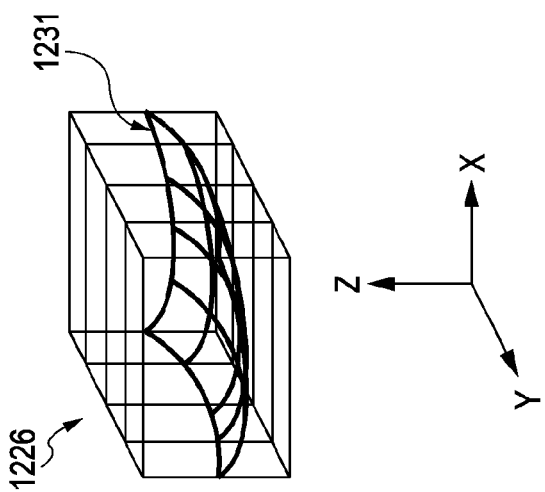
FIGS. 12A to 12C are diagrams for describing steps of estimating a three-dimensional surface in Example 3 of the present invention.
Figure 12B:
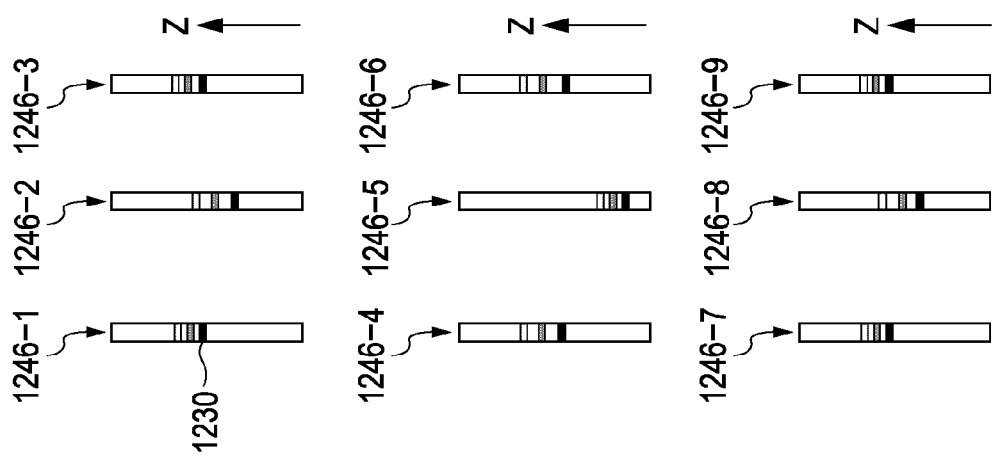
Figure 12A:
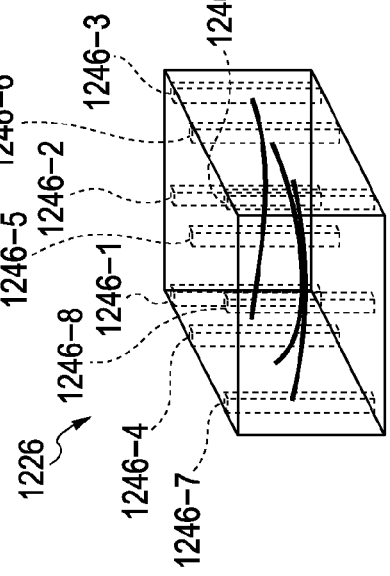

FIGS. 12A to 12C are diagrams for describing steps of estimating a three-dimensional surface in Example 3. In Example 3, a plurality of sampling points are first designated in a region 1226 containing a desired layer.

The sampling points are designated randomly. For example, nine points 1246-1 to 1246-9 shown in FIG. 12A that are evenly arranged in the X- and Y-axis directions can be designated.

The scanning optical system 908 is controlled such that the signal beam 907 is incident at one of the designated sampling points 1246-1 to 1246-9, for example, the point 1246-1.

The scanning optical system 908 is fixed at a position corresponding to the point 1246-1, and the mirror position adjuster 912 is moved, whereby an A-scan image at the point 1246-1 is acquired.

In Example 3, the A-scan image is acquired by moving the mirror position adjuster 912. If an FD-OCT apparatus is used, there is no need to adjust the reference-path length, and information on an A-scan image can be acquired collectively.

Next, the scanning optical system 908 is fixed at another position corresponding to, for example, the point 1246-2, and the mirror position adjuster 912 is moved, whereby an A-scan image at the point 1246-2 is acquired.

Likewise, A-scan images at the points 1246-3 to 1246-9 are acquired. FIG. 12B shows examples of the acquired A-scan images.

The A-scan images each contain a signal representing a portion 1230 of the pigmented layer. Therefore, pieces of position information on the respective portions 1230 are extracted by image processing.

From the positions of the portions 1230 at the sampling points 1246-1 to 1246-9, three-dimensional position information on the pigmented layer, i.e., a surface 1231, is estimated. In accordance with the estimated position information, a C-scan image representing the surface 1231 is acquired, as in Example 1.

Example 4

Example 4, different from Examples 1 to 3, will now be described in which the TD-OCT apparatus according to any of the embodiments of the present invention is applied to eyeground examination. In Example 4, a surface image of the pigmented layer in retinal cells of an eye to be examined is acquired.

Example 4 is basically the same as Example 1, except that the plane along which information is to be acquired is controlled by controlling the position of the entrance pupil.

Figure 13:
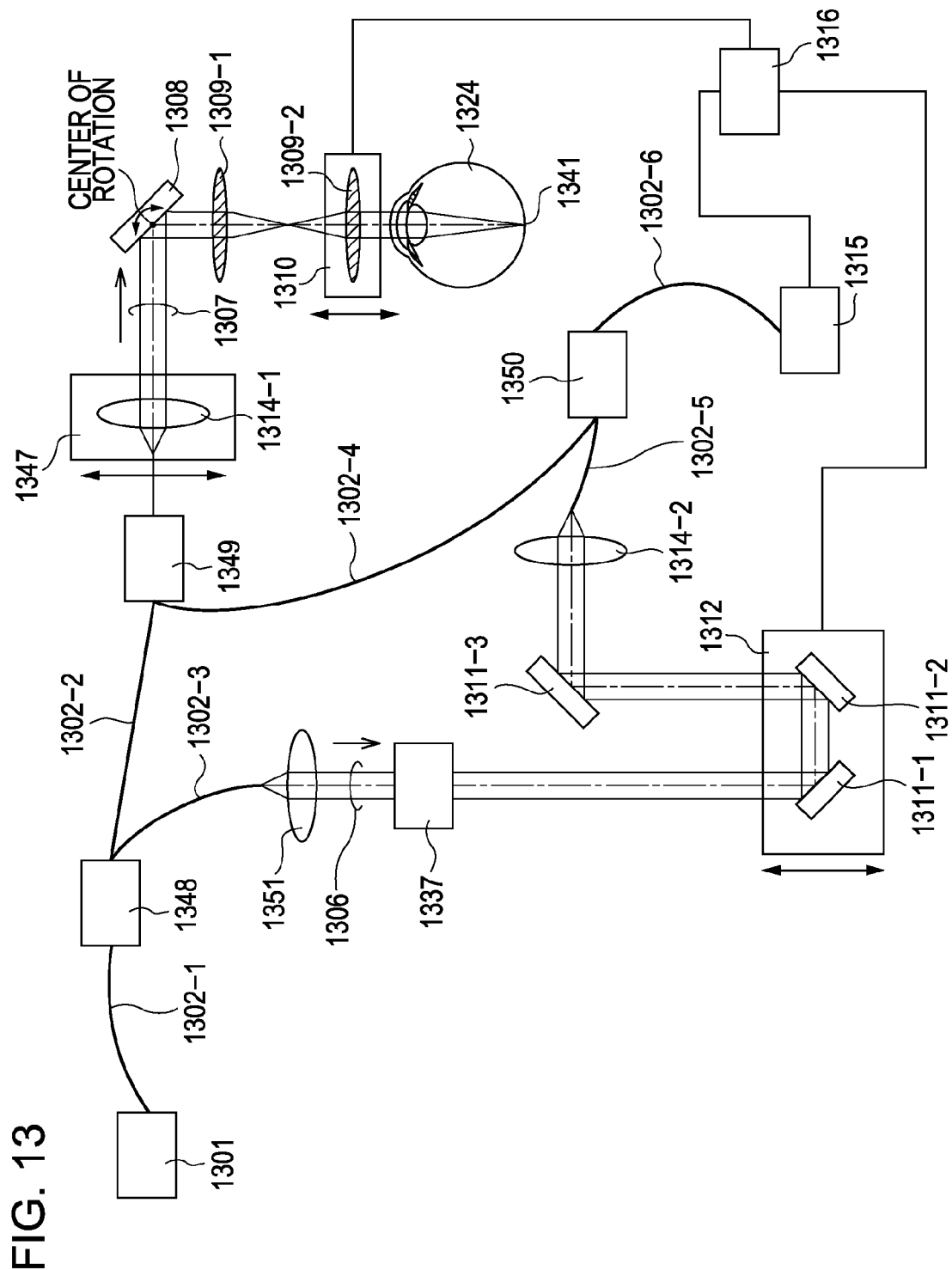
FIG. 13 is a diagram for describing a TD-OCT apparatus and steps of a tomographic imaging method in Example 4 of the present invention.

FIG. 13 is a diagram for describing a TD-OCT apparatus and steps of a tomographic imaging method in Example 4.

In Example 4, a tomogram of the retina is acquired by using the apparatus shown in FIG. 13 in the following manner.

First, light emitted from a light source 1301 is guided through a single-mode optical fiber 1302-1, and is split into a signal beam and a reference beam by a fiber coupler 1348. The light source 1301 is an SLD having a center wavelength of 840 nm and a wavelength width of about 50 nm. The signal beam resulting from the splitting by the fiber coupler 1348 is guided through a single-mode optical fiber 1302-2 to a fiber coupler 1349 and further to a collimator 1314-1, and is converted into a collimated signal beam 1307 by the collimator 1314-1.

The reference beam is guided through a single-mode optical fiber 1302-3 to a collimator 1351 and is output as a collimated reference beam 1306 from the collimator 1351.

The reference beam 1306 is shifted by a frequency shifter 1337 such that the optical frequency thereof is shifted by $\Delta f$, is subsequently reflected by reference mirrors 1311-1 and 1311-2, and is further directed by a reflecting mirror 1311-3 toward a collimator 1314-2.

The positions of the reference mirrors 1311-1 and 1311-2 are controlled by a mirror position adjuster 1312 such that the reference-path length becomes a specific value.

The signal beam 1307 is guided into an examination optical system facing an eye 1324, i.e., an object to be examined. The examination optical system includes a beam guide-splitter, a scanning optical system 1308, a scanning lens 1309-1, and an eyepiece lens 1309-2.

The eyepiece lens 1309-2 is moved in the optical-axis direction of the beam incident thereon by a focus position adjuster 1310.

The scanning optical system 1308 tilts the chief ray of the signal beam 1307 in two directions orthogonal to the optical axis.

Thus, the beam transmitted through the scanning lens 1309-1 and the eyepiece lens 1309-2 is moved so as to have a variable angle with respect to the pupil (iris) of the eye 1324.

Consequently, because of the optical effect of the eye 1324, an eyeground-examination target site 1341 is scanned within a plane (XY plane) on the eyeground, the plane being perpendicular to the optical axis extending in the depth direction.

Some rays of reflections and backscattered light from the target site 1341 return along substantially the same path as the incident path to the target site 1341. Such return rays enter the beam guide-splitter, and some rays thereof are further guided to the collimator 1314-1. Example 4 differs from Example 1 in including a pupil position adjuster 1347 that adjusts the position of the pupil of the collimator 1314-1.

The pupil position adjuster 1347 may be a linear motor stage or the like, or a voice coil motor stage that is movable at a higher speed.

The inclination of the plane along which the eyeground is to be scanned can be controlled, as shown in FIG. 8, by horizontally moving the pupil position adjuster 1347.

The signal beam 1307 condensed by the collimator 1314-1 and the reference beam 1306 condensed by the collimator 1314-2 are combined together by a fiber coupler 1350. The resulting interference beams are converted into electrical signals by a photoelectric conversion detector 1315.

The electrical signals are transmitted to an OCT processing unit 1316.

The composite amplitudes, i.e., the complex amplitudes, of the interference beams obtained by adding the reference beam 1306 and the signal beam 1307 are each an amplitude of heterodyne interference having a carrier frequency corresponding to a frequency difference Δf produced by the frequency shifter 1337.

The wave of the heterodyne interference is an oscillation having a frequency Δf, and the absolute amplitude of the oscillation changes temporally.

The composite amplitudes of the interference beams have temporal oscillations that are in phase opposition. Thus, by the a TD-OCT method, C-scan images (images each extending within an XY plane intersecting the Z-axis direction, i.e., the depth direction) at focal positions at different depths in the object can be acquired.

The process of acquiring a surface image is the same as in Example 1.

In the same manner as in Example 1, first and second B-scan images are acquired. From the first and second B-scan images, information on the three-dimensional surface representing the pigmented layer is estimated.

In accordance with the estimated information on the three-dimensional surface, the scanning optical system 1308 is moved while the pupil position adjuster 1347 is controlled, whereby a C-scan image of the surface 1031 shown in FIG. 10C is acquired.

The plane along which measurement is to be performed is changed by controlling the pupil position adjuster 1347 in accordance with the inclination at each measurement point on the surface 1031. Thus, images composing the curved surface 1031 are successively acquired.

If the mirror position adjuster 1312 is also controlled during the above operation, the desired surface can be measured more precisely.

Example 5

Example 5 will now be described.

Example 5 concerns a case where an object having a simple three-dimensional shape, such as a pipe-like shape, is measured. In this case, position information on the desired layer can be estimated with a single B-scan image.

A tomogram of the retina is acquired by using the apparatus shown in FIG. 9, as in Example 1.

The process of acquiring a tomogram of the retina will now be described.

Figure 14A:
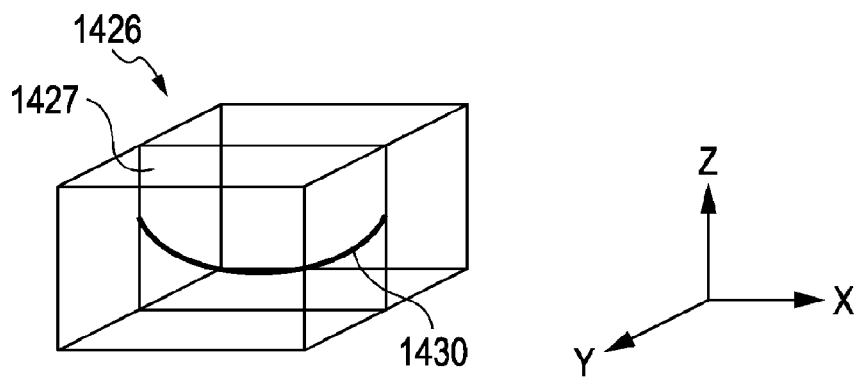
FIGS. 14A to 14C are diagrams for describing steps of estimating a three-dimensional surface in Example 5 of the present invention.
Figure 14B:
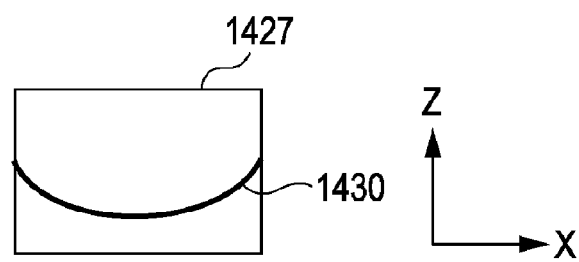
Figure 14C:
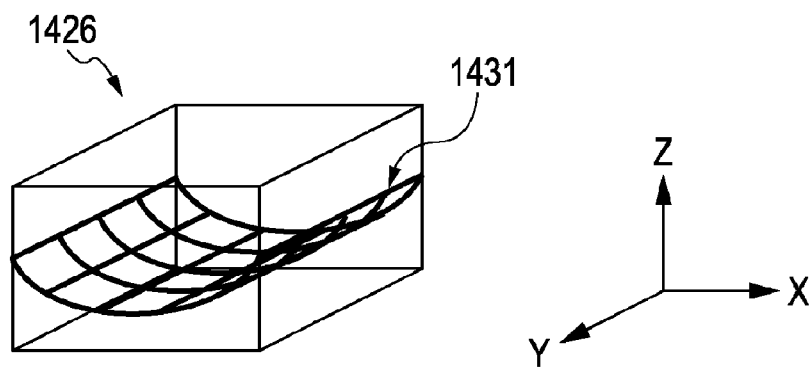

FIGS. 14A to 14C are diagrams for describing steps of estimating a three-dimensional surface in Example 5.

First, a B-scan image of a region 1426 containing a desired layer is acquired.

Specifically, while the mirror position adjuster 912 is moved, the scanning optical system 908 is controlled such that scanning is performed in the X-axis direction in FIG. 14A, whereby a first B-scan image 1427 is acquired.

The first B-scan image 1427 contains a portion 1430 of the desired layer. Position information on the portion 1430 is extracted by image processing.

In Example 5, the depth position does not change with the change in the Y-axis-direction position. Therefore, only with the position information on the portion 1430, three-dimensional position information on a surface 1431 can be calculated.

For example, if the portion 1430 is fitted to a function of $Z=X^2$, the surface 1431 is also expressed as $Z=X^2$.

In accordance with the position information acquired in this manner, a C-scan image of the surface 1431 is acquired, as in Example 1.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

This application claims the benefit of Japanese Patent Application No. 2008-331879 filed Dec. 26, 2008, which is hereby incorporated by reference herein in its entirety.

What is claimed is:

1. An optical tomographic imaging method in which light from a light source is split into a measuring beam and a reference beam, the measuring beam being moved by a scanning optical system and guided to an object to be examined, the reference beam being guided to a reference mirror, and in which a tomogram of the object is generated from a return beam of the measuring beam reflected or scattered by the object and the reference beam reflected by the reference mirror, the method comprising:
acquiring longitudinal sectional information on the object;
calculating depth-position information on the object from the longitudinal sectional information; and acquiring a three-dimensional surface image of the object by controlling a reference-path length defined by the reference mirror and a scanning operation of the scanning optical system in accordance with the depth-position information on the object.

2. The optical tomographic imaging method according to claim 1, wherein the longitudinal sectional information on the object is a longitudinal sectional image of the object.

3. The optical tomographic imaging method according to claim 2, wherein the longitudinal sectional image of the object includes at least two longitudinal sectional images of the object substantially orthogonal to each other.

4. The optical tomographic imaging method according to claim 2, wherein the longitudinal sectional image of the object includes at least two longitudinal sectional images of the object substantially parallel to each other.

5. The optical tomographic imaging method according to claim 1, wherein the longitudinal sectional information on the object is calculated from a plurality of pieces of one-dimensional information on the object.

6. The optical tomographic imaging method according to claim 1, wherein, in acquiring the three-dimensional surface image of the object, a point in the object at which the measuring beam is incident is controlled instead of controlling the reference-path length defined by the reference mirror.

7. The optical tomographic imaging method according to claim 1, wherein the object is a set of retinal cells in an eye, and the depth-position information on the object is position information on a three-dimensional surface in the retinal cells.

8. An optical tomographic imaging apparatus in which light from a light source is split into a measuring beam and a reference beam, the measuring beam being guided to an object to be examined, the reference beam being guided to a reference mirror, and in which a tomogram of the object is generated from a return beam of the measuring beam reflected or scattered by the object and the reference beam reflected by the reference mirror, the apparatus comprising:
- a scanning optical system capable of moving the measuring beam in one-dimensional and two-dimensional manners;
- a reference-path-length adjuster provided to the reference mirror and configured to adjust an optical-path length of the reference beam; and
- a control unit configured to control the reference-path-length adjuster and the scanning optical system so that a three-dimensional surface image of the object is acquired in accordance with depth-position information on the object estimated in advance.

9. The optical tomographic imaging apparatus according to claim 8,
wherein the reference-path-length adjuster includes
- a stage capable of coarse adjustment and used in acquiring the depth-position information; and
- a stage capable of fine adjustment and used in acquiring the three-dimensional surface image.

* * * * *